(12) United States Patent
DiBiasi et al.

(10) Patent No.: US 8,632,494 B2
(45) Date of Patent: Jan. 21, 2014

(54) REVERSIBLE CAP FOR PEN NEEDLE OUTER COVER

(75) Inventors: Michael A. DiBiasi, West Milford, NJ (US); Robert Banik, Long Valley, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 72 days.

(21) Appl. No.: 13/373,150

(22) Filed: Nov. 7, 2011

(65) Prior Publication Data
US 2012/0059331 A1 Mar. 8, 2012

Related U.S. Application Data (63) Continuation of application No. 12/563,096, filed on Sep. 18, 2009, now Pat. No. 8,133,200.

(51) Int. Cl.
*A61M 5/00* (2006.01)
(52) U.S. Cl.
USPC .......................... 604/111; 604/110; 604/93.01

(58) Field of Classification Search
USPC ......... 604/192–198, 163, 263, 110, 171, 111; 206/363–366; 600/576
See application file for complete search history.

(56) References Cited

U.S. PATENT DOCUMENTS

| | | |
|---|---|---|
| 3,149,717 A | 9/1964 | Castelli |
| 3,968,914 A | 7/1976 | Goncalves |
| 4,643,199 A | 2/1987 | Jennings |
| 5,205,408 A | 4/1993 | Cobb |
| 2002/0133122 A1* | 9/2002 | Giambattista et al. ........ 604/198 |
| 2006/0032769 A1 | 2/2006 | Erickson |
| 2006/0253103 A1 | 11/2006 | Utterberg |
| 2008/0179207 A1 | 7/2008 | Stowe |

* cited by examiner

*Primary Examiner* — Nicholas Lucchesi
*Assistant Examiner* — Leah Stohr
(74) *Attorney, Agent, or Firm* — Roylance, Abrams, Berdo & Goodman, L.L.P.

(57) ABSTRACT

A pen needle assembly includes a cap for covering the non-injection end of a needle of a pen needle. The needle is received by a hub, which is disposed in an outer cover. The cap is adapted to be connected to the outer cover in a first or second position. The cap is removable in the first position and the cap is locked to the outer cover in the second position.

19 Claims, 9 Drawing Sheets

REVERSIBLE CAP FOR PEN NEEDLE OUTER COVER

CROSS REFERENCE TO RELATED APPLICATION

This application is a continuation of U.S. patent application Ser. No. 12/563,096, filed Sep. 18, 2009 now U.S. Pat. No. 8,113,200, the entire disclosure of said prior application being incorporated herein by reference.

FIELD OF THE INVENTION

The present invention relates to a reversible cap for covering a non-patient end of the needle. More particularly, the present invention relates to a reversible cap that provides a sharps container when connected to an outer cover.

BACKGROUND OF THE INVENTION

In certain circumstances, it is desirable to inject medication directly into human tissue. Typically, syringes or pen injection devices are used to inject medicaments into tissue areas, such as the intramuscular tissue layer, the subcutaneous tissue layer, and the intradermal tissue layer.

Figure 1:
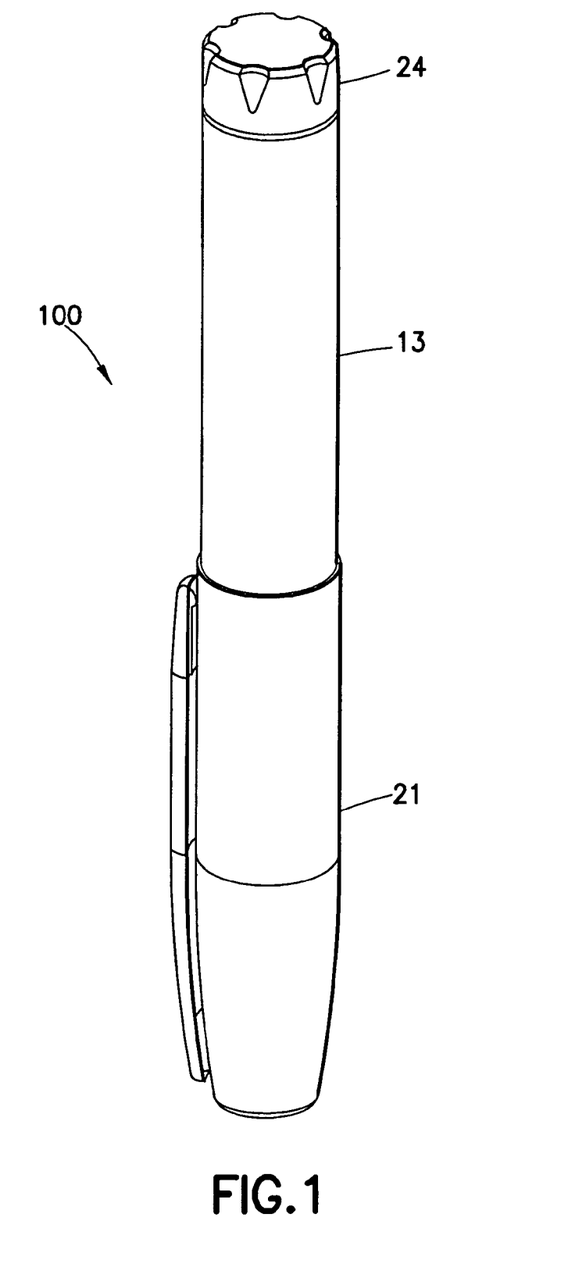
FIG. 1 is a perspective view of an assembled existing pen needle assembly.
Figure 2:
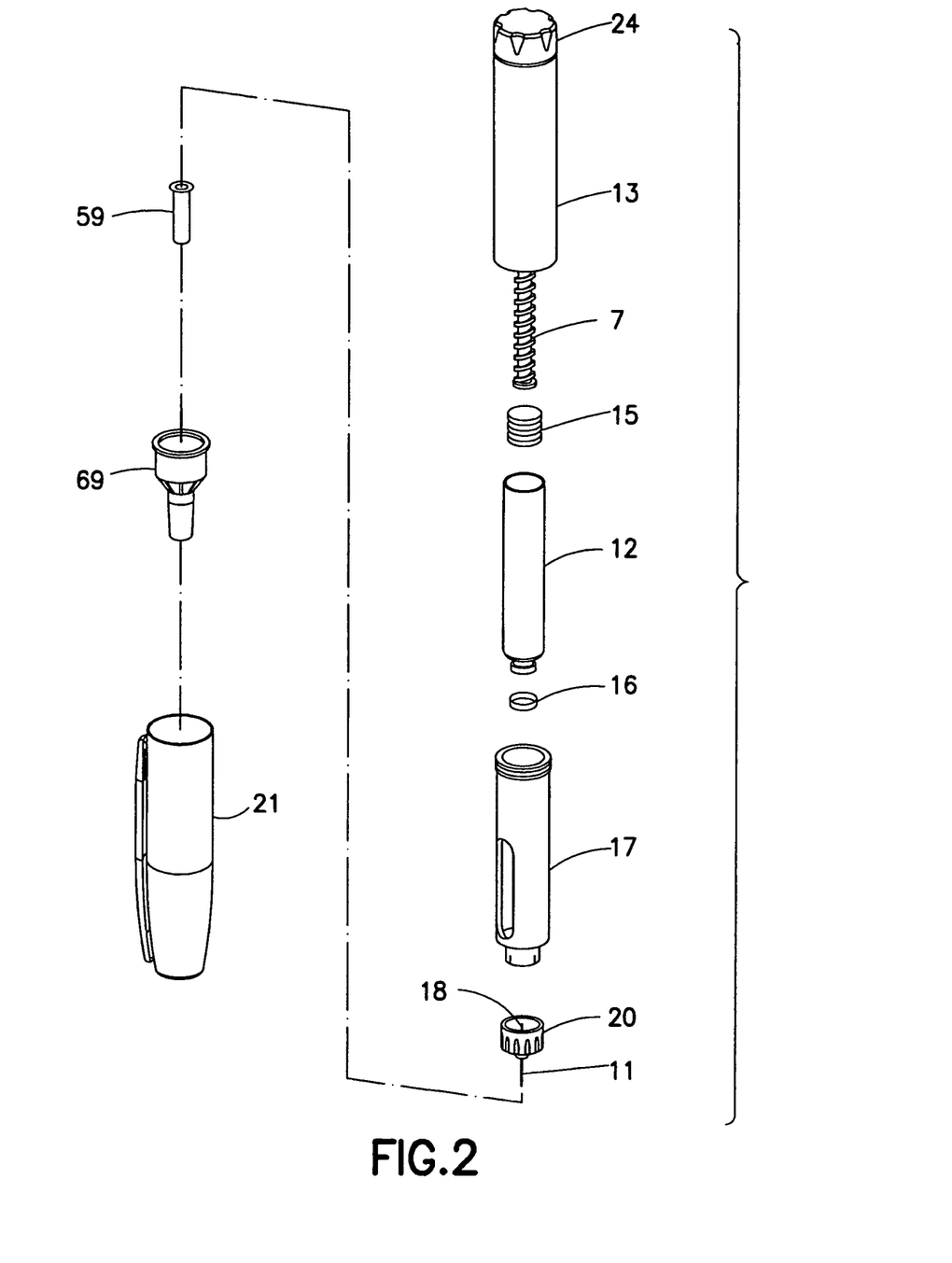
FIG. 2 is an exploded perspective view of the components of the pen needle assembly of FIG. 1.

The assembly and operation of a typical pen injection device, as shown in FIGS. 1 and 2, is described in U.S. Patent Application Publication No. 2006/0229562, published on Oct. 12, 2006, Now U.S. Pat. No. 7,645,264, issued Jan. 12, 2010, both of which are hereby incorporated by reference in their entirety.

Pen injection devices, such as the exemplary pen injector 100, as shown in FIG. 1, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the pen injector device 100 in a shirt pocket, purse or other suitable location.

FIG. 2 is an exploded view of an exemplary drug delivery pen shown in FIG. 1. The dose knob/button 24 has a dual purpose and is used to both set the dosage of the medication to be injected and to inject the dosed medicament via the lead screw 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used such as attaching to the cartridge. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle 11 by any suitable means, such as an interference fit or a snap fit. The outer cover 69 and inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

A pen needle, which includes the hub 20, needle 11, outer shield 69 and inner shield 59, is typically used for a single injection and is then disposed of. Following an injection, the used needle, or "sharps", must be properly disposed of. Used sharps may become contaminated by body fluids and the like creating a hazard for anyone that may handle them following their use. Sharps disposal containers store the disposed sharps and prevent unintentional contact with any object disposed therein. Accordingly, a need exists for a cap for an outer cover that completely encapsulates the pen needle within a puncture resistant cover and cap after use.

Another problem is properly handling a used needle while avoiding an accidental needle stick or contamination. Pen needle outer covers are typically sealed by a foil seal that is discarded after opening the outer cover to access the hub assembly. Accordingly, a need exists for a cap that seals the outer cover both before and after using the needle.

SUMMARY OF THE INVENTION

In accordance with an aspect of the present invention, a reversible cap connects to an outer cover in a first position before the needle is used and in a second position after the needle is used.

In accordance with another aspect of the present invention, opposite faces of the cap have different indicia to indicate the condition of the pen needle contained therein.

A pen needle assembly according to an exemplary embodiment of the present invention includes a cap for covering the non-injection end of a needle of a pen needle. The needle is received by a hub, which is disposed in an outer cover. The cap is adapted to be connected to the outer cover in a first or second position. The cap is removable in the first position and the cap is locked to the outer cover in the second position.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which.

Throughout the drawings, like reference numbers will be understood to refer to like parts, components and structures.

DETAILED DESCRIPTION OF THE EXEMPLARY EMBODIMENTS

Figure 3:
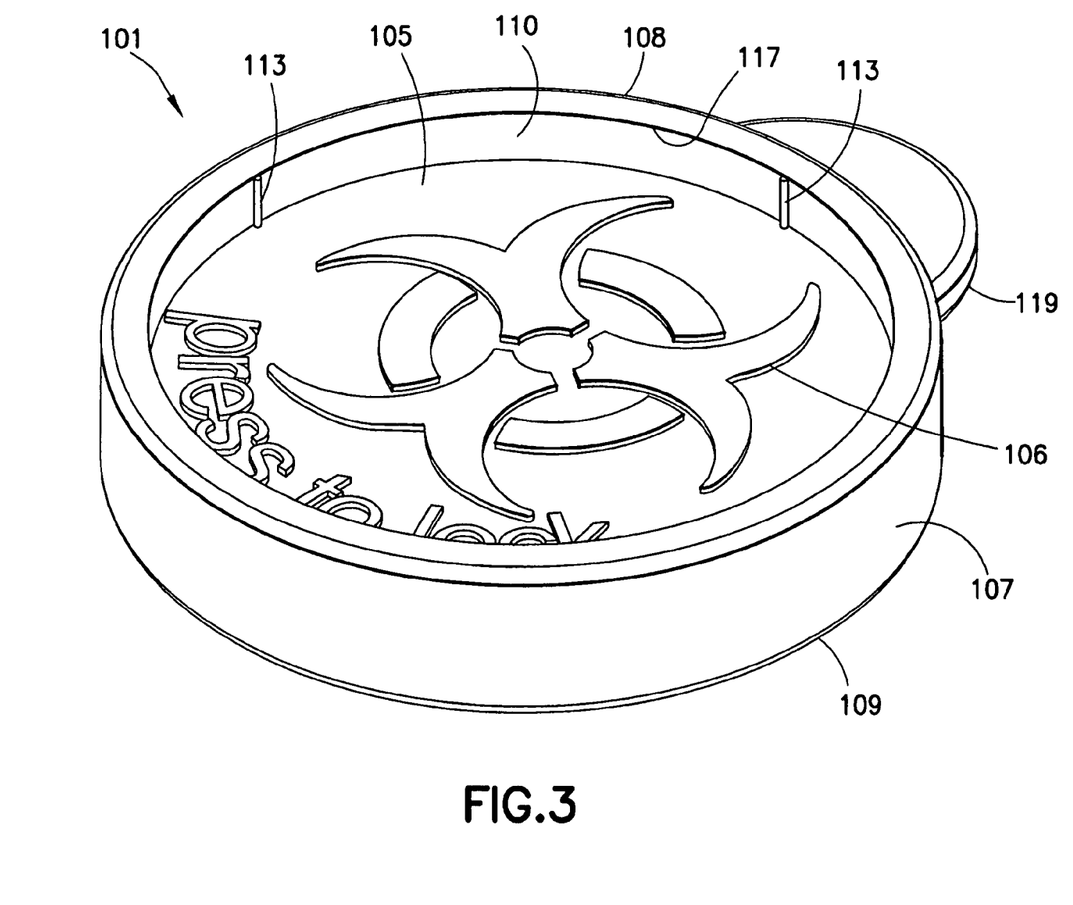
FIG. 3 is a perspective view of a reversible cap for a pen needle outer cover according to an exemplary embodiment of the present invention.
Figure 4:
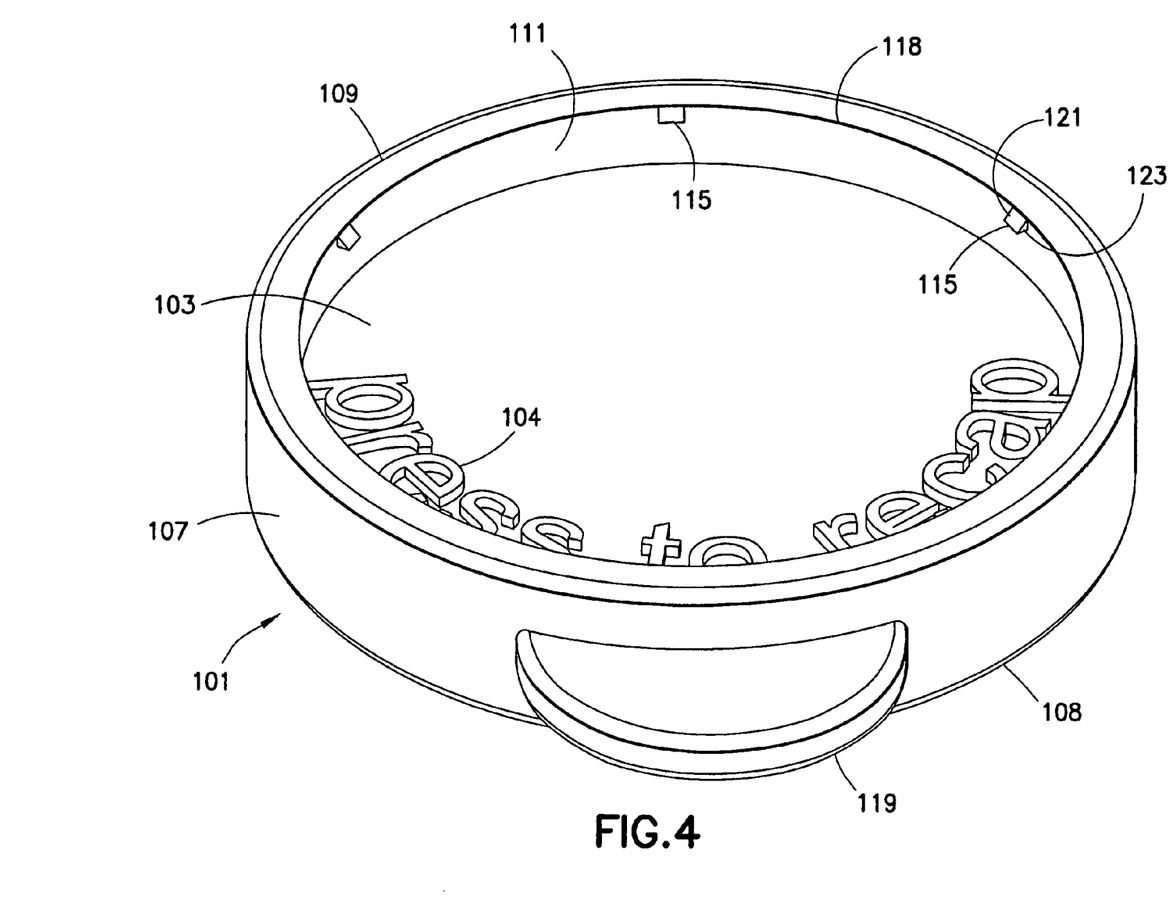
FIG. 4 is a perspective view of the other side of the reversible cap of FIG. 3.

In an exemplary embodiment of the present invention, as shown in FIGS. 3-6, a cap 101 covers a non-patient end 147 of the needle 149 of the pen needle 141 before and after using the needle for an injection. The cap 101 has a first surface 103 and a second surface 105. The cap 101 is connectable to an outer cover 169 of the pen needle 141 in either a first position in which the first surface is visible as shown in FIG. 3 or in a second position in which the second position is visible as shown in FIG. 4. The first surface 103 has indicia 104 indicating that the needle 103 has not yet been used for an injection. The second surface 105 has indicia 106, such as a contaminated sharps symbol, indicating that the needle has been used for an injection.

The cap 101 has an outer side wall 107 having a first end 108 and a second end 109. A first lip 117 extends inwardly from the first end 108 of the side wall 107, and a second lip 118 extends inwardly from a second end 109 of the side wall 107. A first inner side wall 110 extends from the second surface 105 to the first end. A second inner side wall 111 extends from the first surface 103 to the second end 109. A plurality of ribs 113 extend axially along the first inner side wall 110. The ribs 113 extend from the second surface 105 to the first lip 117. A plurality of tabs 115 are disposed circumferentially around the second inner side wall 111. A handle 119 extends outwardly from the outer side wall 107 to facilitate gripping the cap 101.

Figure 5:
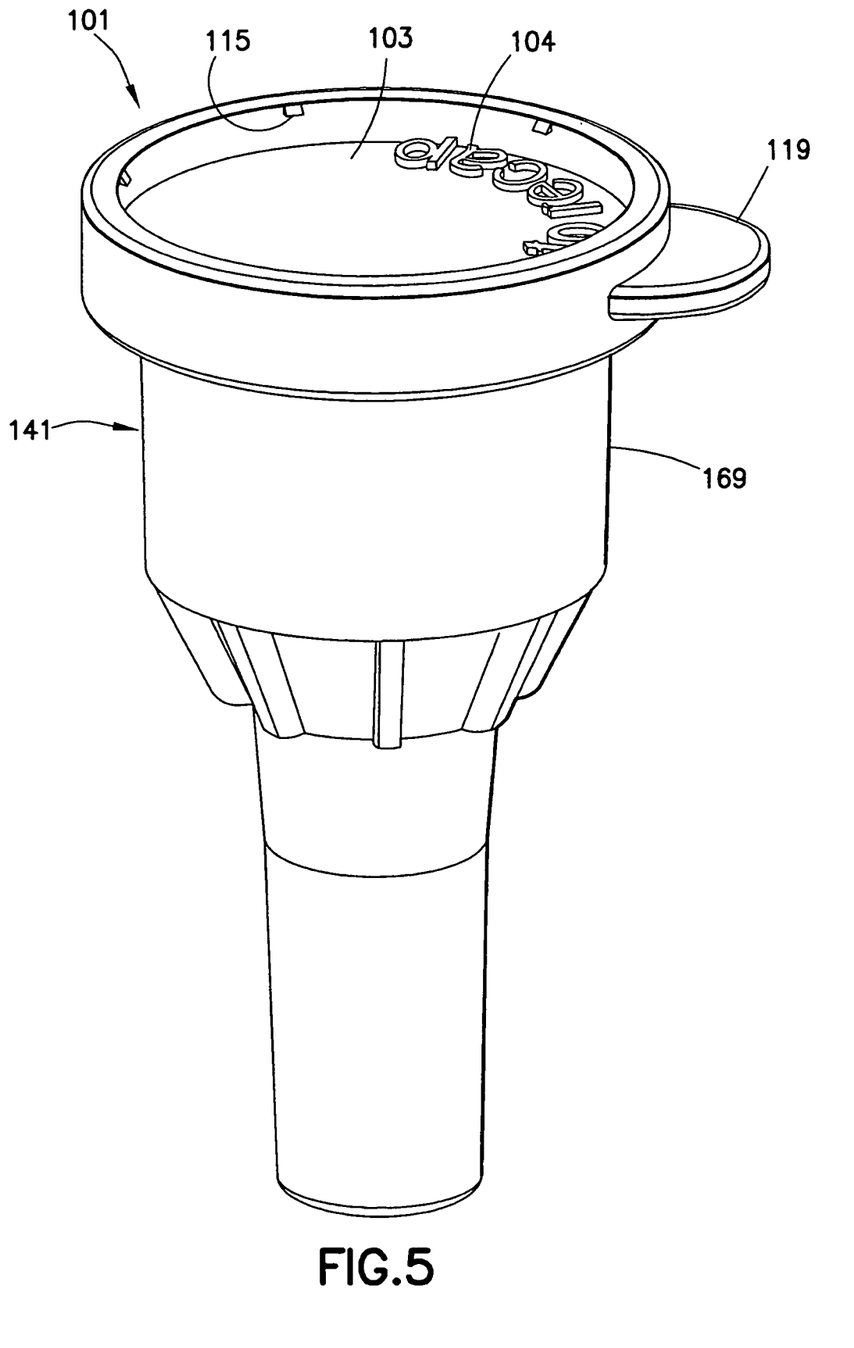
FIG. 5 is a perspective view of the cap of FIG. 3 connected to an outer cover.

The cap 101 is initially connected to the outer cover 169 in a first position, as shown in FIG. 5, such that the first surface 103 is visible. The indicia 104 on the first surface 103 indicate that the needle has not yet been used for an injection. The ribs 113 create an interference fit with the flange 171 of the outer cover 169. When an injection is to be made, a user grips the handle 119 and lifts the handle away from the outer cover 169, thereby removing the cap 101 from the outer cover. The pen needle 151 may then be connected to a pen injection device 100 (FIGS. 1 and 2) to perform an injection.

Figure 6:
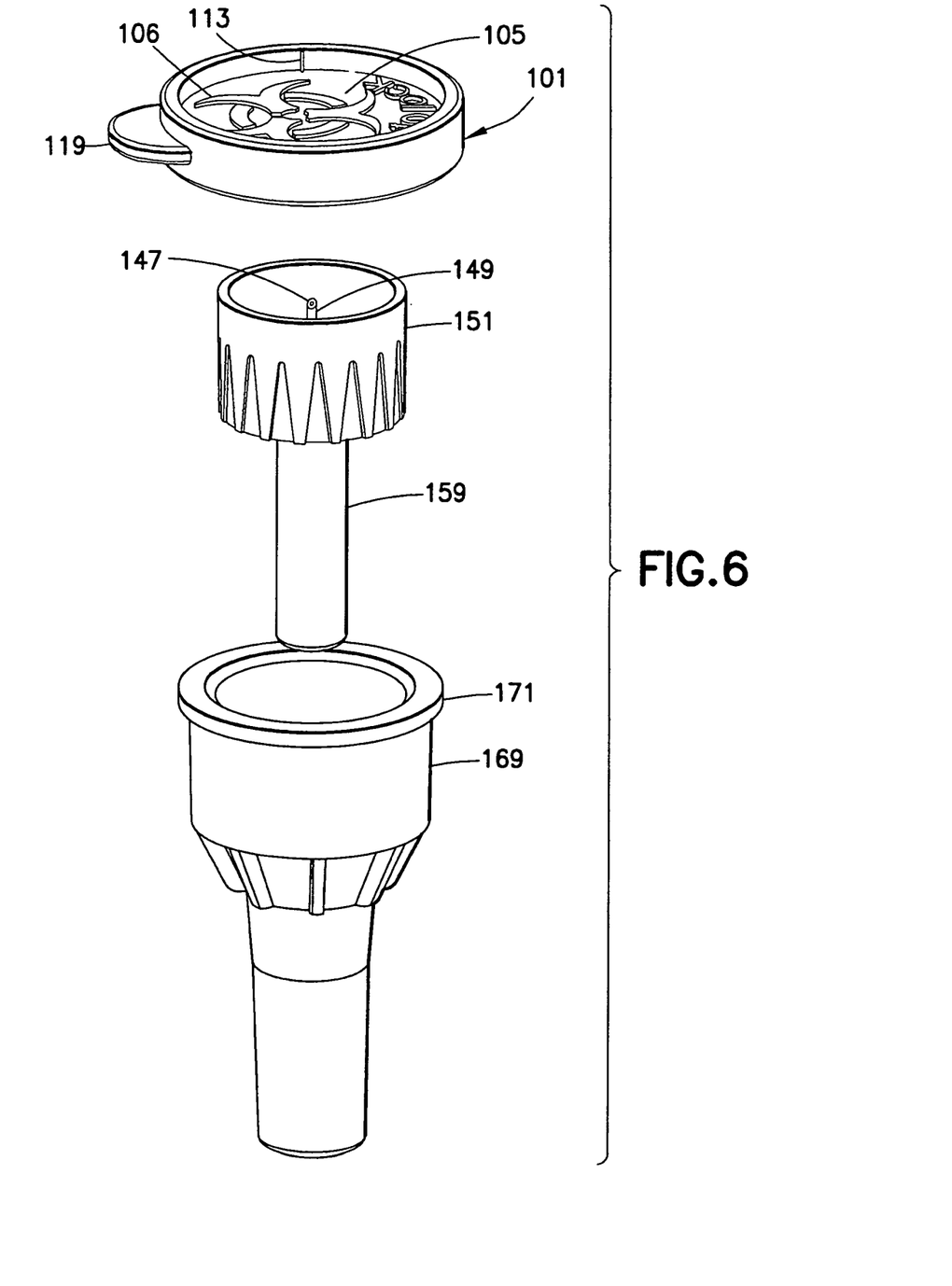
FIG. 6 is an exploded perspective view of cap and pen needle of FIG. 5 in which the cap has been reversed.

After injecting a medicament, an inner shield 159 may optionally be disposed over the patient end of the needle 149 to shield the patient-end of the needle and prevent an accidental needle stick. The hub 151 and inner shield 159, if used, are then disposed in the outer cover 169. The cap 101 is reversed and connected to the outer cover 169 in a second position, as shown in FIG. 6. As the cap 101 is pushed downwardly on the outer cover 169, the sloped portion 121 of the tabs 115 pass over the flange 171, thereby locking the flange between the tabs 115 and the first surface 103 of the cap 101. The flat portion 123 of the tab 115, which is substantially parallel to the first surface 103, prevents the tab 115 from passing over the flange 171, thereby securely locking the cap 101 to the outer cover 169 and providing a sharps container. The second indicia 106 on the second surface 105 of the cap 101 is visible when the cap 101 is locked in the second position. The second indicia 106 indicate that the needle has been used for an injection, and such indicia could include a contaminated sharps symbol, as shown in FIG. 3.

In another exemplary embodiment, as shown in FIGS. 7-14, a reversible cap 201 is connectable to an outer cover 169 (FIG. 6) of a pen needle in a first or second position. The cap 201 has a first surface 203 that is visible when the cap 201 is connected to the outer cover in the first position. A second surface 205 of the cap 201 is visible when the cap is connected to the outer cover in the second position.

Figure 7:
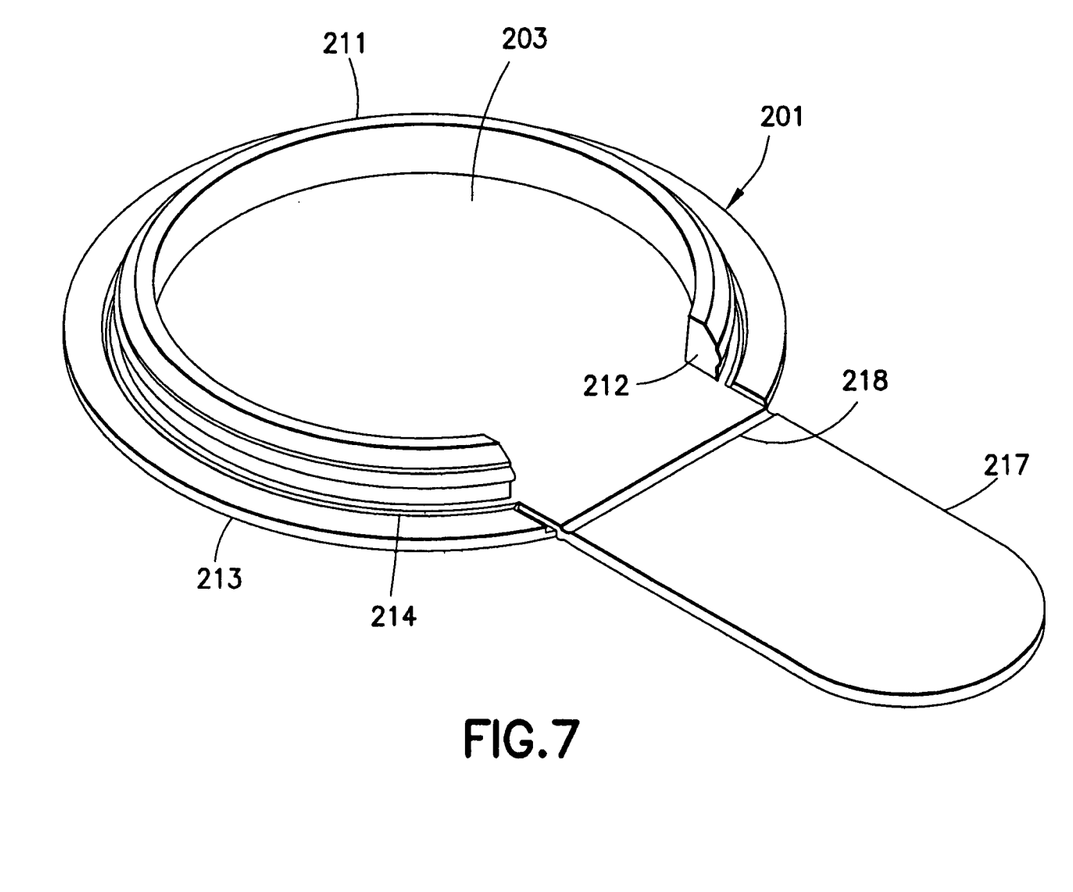
FIG. 7 is a perspective view of a reversible cap according to another exemplary embodiment of the present invention.
Figure 8:
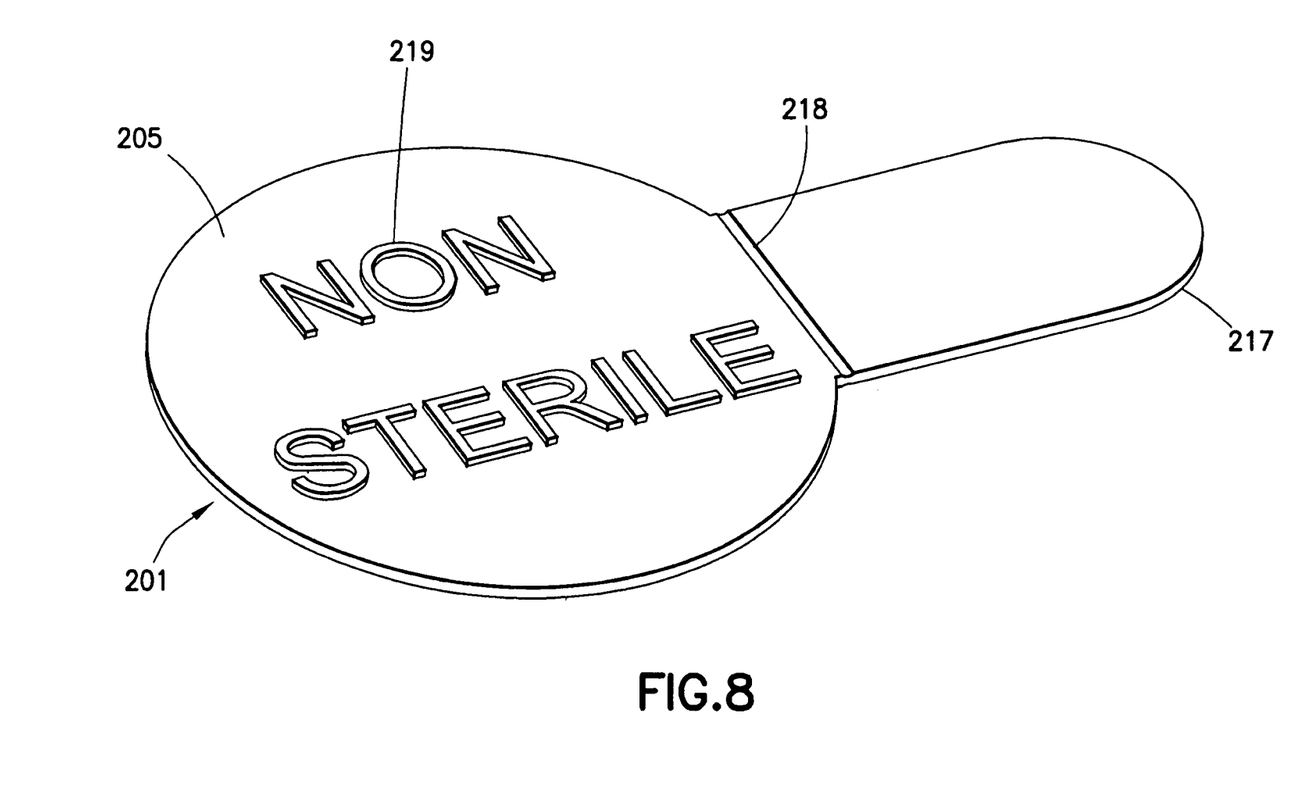
FIG. 8 is a perspective view of the other side of the reversible cap of FIG. 7 with the removable flange removed.

A sealing wall 211 extends upwardly from the first surface 203 of the cap 201, as shown in FIG. 7. An opening 212 is formed in the wall 211. A removable flange 213 surrounds the sealing wall 211. A notch 214 is formed between the flange 213 and the first surface 203 to facilitate removing the flange 213. A tab 217 extends outwardly from the first surface 203 and is preferably substantially planar with the first surface 203. A groove 218 is formed in the tab 217 to facilitate flexing of the tab about the groove 218. Indicia 219 are disposed on the second surface 205 of the cap 201, as shown in FIG. 8, to indicate that the outer cover has been opened.

Figure 9:
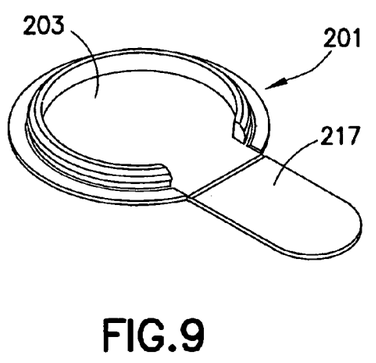
FIG. 9 is a perspective view of the cap of FIG. 7.
Figure 10:
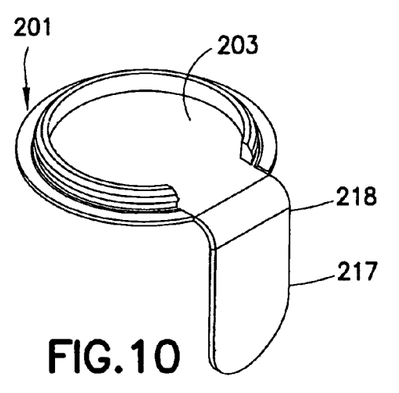
FIG. 10 is a perspective view of the cap of FIG. 7 sealed to an outer cover.

FIGS. 9-14 illustrate opening and resealing the outer cover 169 with the cap 201, as shown in FIG. 9. The cap 201 is connected to the outer cover during the manufacturing process. The removable flange 213 of the cap 201 is connected to the flange 171 of the outer cover 169, preferably by ultrasonic welding or bonding, in the first position such that the first surface 203 is visible, as shown in FIG. 10. The tab 217 is bent around the groove 218 such that the tab is adjacent the outer cover.

Figure 11:
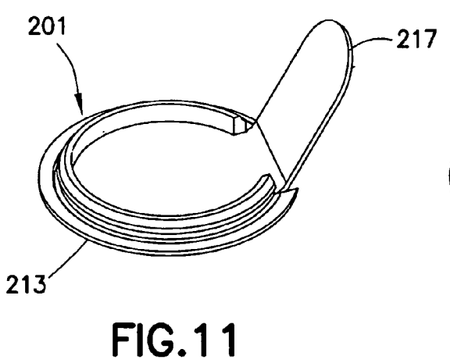
FIG. 11 is a perspective view of the cap of FIG. 7 in which the tab is lifted to break the seal with the outer cover.
Figure 12:
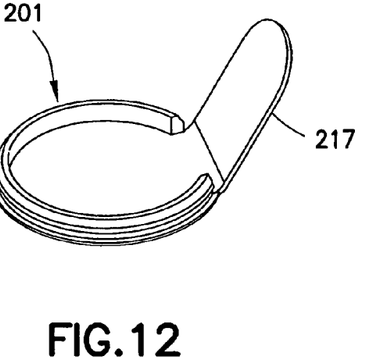
FIG. 12 is a perspective view of the cap of FIG. 7 after having been removed from the outer cover.
Figure 13:
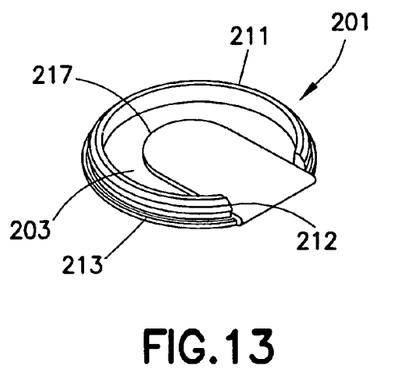
FIG. 13 is a perspective view of the cap of FIG. 7 with the tab secured to a first face of the cap.
Figure 14:
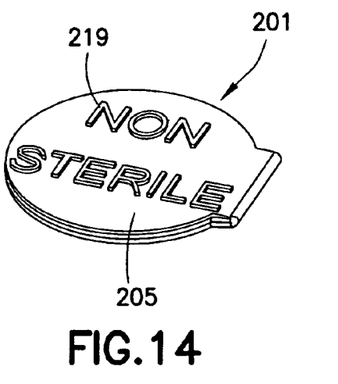
FIG. 14 is a perspective view of the cap of FIG. 7 showing a second face thereof.

When the outer cover is to be opened the tab 217 is lifted upwardly and away from the outer cover, as shown in FIG. 11. The flange 213 is then separated from the cap 201 along the notch 214, thereby breaking the seal between the cap 201 and the outer cover. The cap 201 is then removed from the outer cover and the tab 217 is pushed downwardly toward the first surface 203 of the cap 201, as shown in FIG. 13, and the tab 217 is received by the opening 212 in the sealing wall 211. When the injection has been made and the used pen needle is returned to the outer cover, the cap 201 is connected to the outer cover in the second position such that the second surface 205 is visible. The cap 201 is pushed downwardly such that the sealing wall 211 forms a seal with the outer cover. In the second position, the indicia 219 on the second surface 205 of the cap 201 is visible to indicate that the pen needle has been used for an injection. Such indicia could include "NON STERILE", as shown in FIGS. 8 and 14, but any suitable indicia may be used.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

What is claimed is:

1. A pen needle assembly, comprising:
a needle;
a hub for receiving said needle;

an outer cover for receiving said hub prior to and after an injection, said hub being removed from said outer cover for an injection; and a cap adapted to be connected to said outer cover in a first or second position, said cap being removable in said first position and said cap being locked to said outer cover in said second position, said cap being reversed in said second position relative to said first position, and said cap having first and second surfaces having different indicia thereon indicating whether said cap is connected to said outer cover in said first or second position.

2. The pen needle assembly of claim 1, wherein
a plurality of ribs extend axially along a first inner side wall of said cap to facilitate connecting said cap to said outer cover in said first position.

3. The pen needle assembly of claim 1, wherein
a plurality of tabs are disposed on a second inner side wall of said cap to lockably receive a flange of said outer cover in said second position.

4. The pen needle assembly of claim 1, wherein
a handle extends outwardly from said cap.

5. The pen needle assembly of claim 1, wherein
said indicia indicating that said cap is in said second position comprises a contaminated sharps symbol.

6. The pen needle assembly of claim 1, wherein
said indicia indicating that said cap is in said first position indicates that said needle has not been used for an injection.

7. A reversible cap for a pen needle outer cover, comprising:
a base having a first surface and a second surface;
a first inner side wall extending substantially perpendicularly from said second surface;
a second inner side wall extending substantially perpendicularly from said first surface, said cap being connectable to an outer cover of a pen needle in a first position such that said first surface is visible or in a second position such that said second surface is visible, the pen needle being received by said outer cover prior to and after an injection and removed from said outer cover for an injection; and
a handle connected to said base to facilitate handling said cap in said first and second positions.

8. The reversible cap of claim 7, wherein
a plurality of ribs extend axially along said first inner side wall to facilitate connecting said cap to the outer cover in said first position.

9. The reversible cap of claim 7, wherein
a plurality of tabs are disposed on said second inner side wall of said cap to lockably receive a flange of the outer cover in said second position.

10. The reversible cap of claim 7, wherein
first indicia disposed on said first surface indicating that said cap is in said first position and that said needle has not been used for an injection.

11. The reversible cap of claim 7, wherein
second indicia disposed on said second surface indicating that said cap is in said second position.

12. The reversible cap of claim 11, wherein
said second indicia comprises a contaminated sharps symbol.

13. A pen needle assembly, comprising:
a needle;
a hub for receiving said needle;
an outer cover for receiving said hub prior to and after an injection, said hub being removed from said outer cover for an injection;
a cap adapted to be connected to said outer cover in a first or second position, said cap being removable in said first position and said cap being locked to said outer cover in said second position, and said cap being reversed in said second position relative to said first position; and
a plurality of ribs extending axially along a first inner side wall of said cap to facilitate connecting said cap to said outer cover in said first position.

14. The pen needle assembly of claim 13, wherein
a plurality of tabs are disposed on a second inner side wall of said cap to lockably receive a flange of said outer cover in said second position.

15. The pen needle assembly of claim 13, wherein
a handle extends outwardly from said cap.

16. A pen needle assembly, comprising:
a needle;
a hub for receiving said needle;
an outer cover for receiving said hub prior to and after an injection, said hub being removed from said outer cover for an injection;
a cap adapted to be connected to said outer cover in a first or second position, said cap being removable in said first position and said cap being locked to said outer cover in said second position, and said cap being reversed in said second position relative to said first position; and
a plurality of tabs disposed on a second inner side wall of said cap to lockably receive a flange of said outer cover in said second position.

17. The pen needle assembly of claim 16, wherein
a handle extends outwardly from said cap.

18. A pen needle assembly, comprising:
a needle;
a hub for receiving said needle;
an outer cover for receiving said hub prior to and after an injection, said hub being removed from said outer cover for an injection;
a cap adapted to be connected to said outer cover in a first or second position, said cap being removable in said first position and said cap being locked to said outer cover in said second position, and said cap being reversed in said second position relative to said first position; and
a handle extending outwardly from said cap.

19. The pen needle assembly of claim 18, wherein
a plurality of tabs are disposed on a second inner side wall of said cap to lockably receive a flange of said outer cover in said second position.

* * * * *